(12) United States Patent
Wakabayashi

(10) Patent No.: US 7,616,803 B2
(45) Date of Patent: Nov. 10, 2009

(54) SURFACE INSPECTION METHOD AND APPARATUS

(75) Inventor: Akihiro Wakabayashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 645 days.

(21) Appl. No.: 11/052,895

(22) Filed: Feb. 9, 2005

(65) Prior Publication Data

US 2006/0110024 A1    May 25, 2006

(30) Foreign Application Priority Data

Nov. 22, 2004    (JP) ............................. 2004-337053

(51) Int. Cl.
  *G06K 9/00*   (2006.01)
  *H04N 7/18*   (2006.01)
  *H04N 9/47*   (2006.01)

(52) U.S. Cl. ...................................... 382/141; 348/125

(58) Field of Classification Search ................. 382/141, 382/149; 348/125; 700/110; 356/237.1
See application file for complete search history.

(56) References Cited

U.S. PATENT DOCUMENTS 4,972,493 A * 11/1990 Chemaly .................... 382/149
5,379,347 A     1/1995 Kato et al.
6,295,374 B1 *  9/2001 Robinson et al. ............ 382/218

FOREIGN PATENT DOCUMENTS

| JP | 6-249792 | 9/1994 |
|---|---|---|
| JP | 6-76849 | 10/1994 |
| JP | 10-103938 | 4/1998 |
| JP | 2000-47369 | 2/2000 |
| JP | 2000-171403 | 6/2000 |

* cited by examiner

*Primary Examiner*—Samir A Ahmed
*Assistant Examiner*—Li Liu
(74) *Attorney, Agent, or Firm*—Kratz, Quintos & Hanson, LLP

(57) ABSTRACT

There have been disclosed a surface inspection method and a surface inspection apparatus for inspecting the surface of an article, the surface being almost flat and continuous and having non-flat parts with convex shapes and concave shapes provided based on specifications, capable of inspecting for defective parts in the non-flat parts without detecting the non-flat parts as defective parts. The surface inspection apparatus comprises an image pickup device, a correction data calculation unit for calculating non-flat part correction data for making the image of the non-flat part into one equivalent to the image of the flat part based on the difference between the image of the non-flat part and the image of the flat part, a non-flat correction unit for correcting the image of the non-flat part based on the non-flat part correction data, and a defect detection unit for detecting defects on the article surface by processing the image of the article surface after correcting the image of the non-flat part.

14 Claims, 7 Drawing Sheets

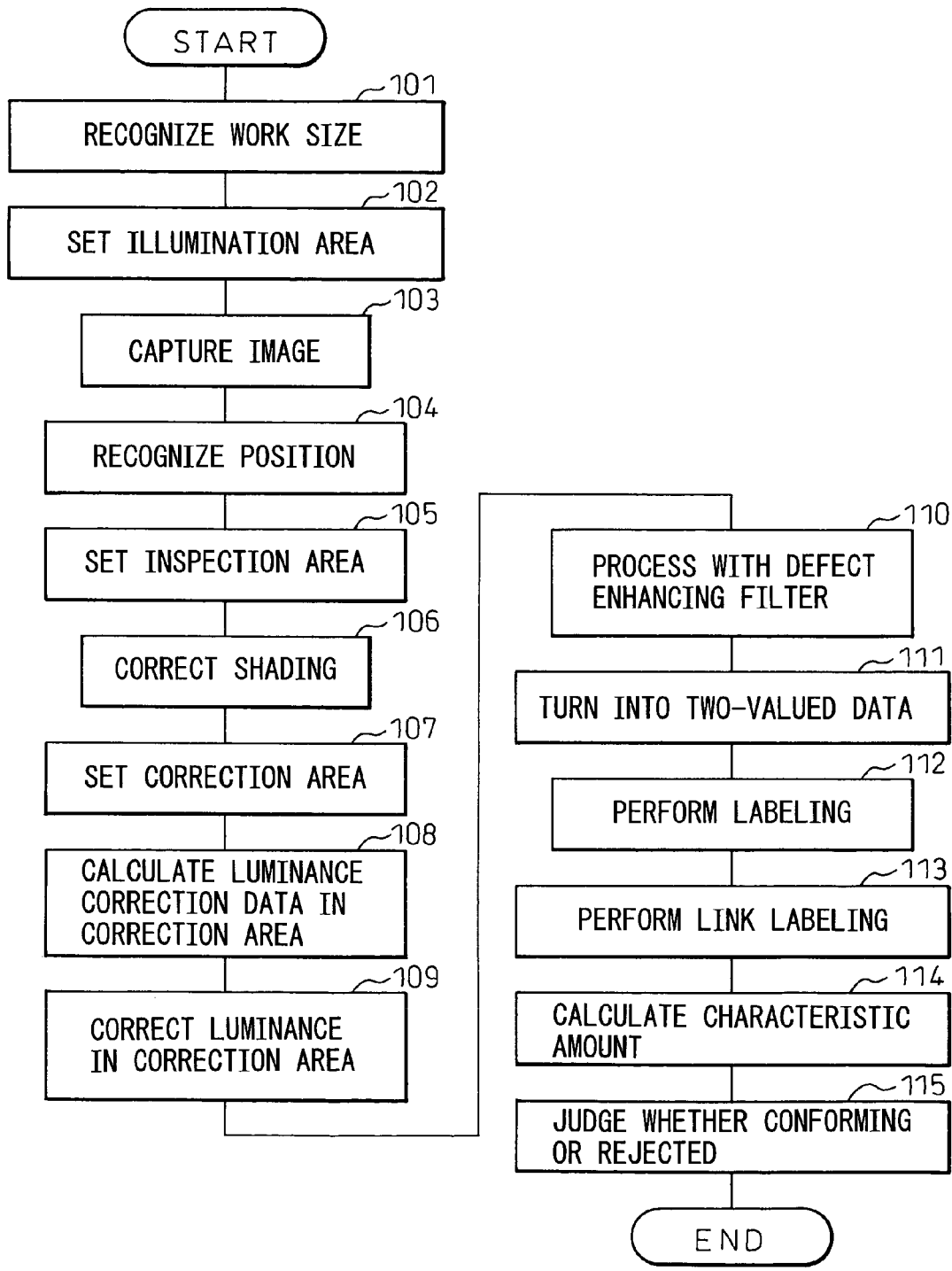

A—A

FIG.7A
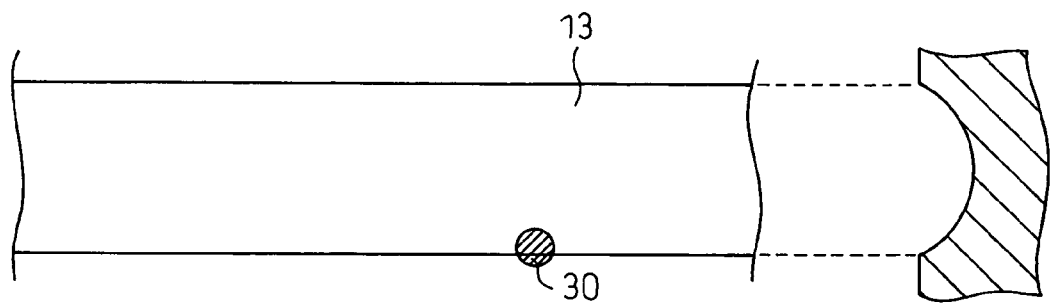
FIG.7B
FIG.7C
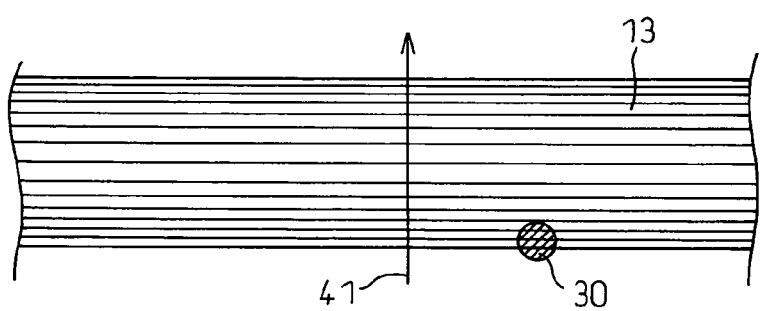 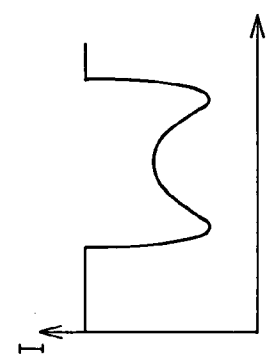
FIG.7D
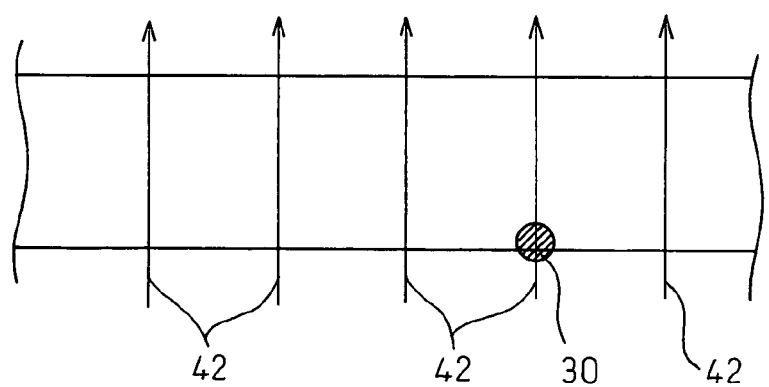

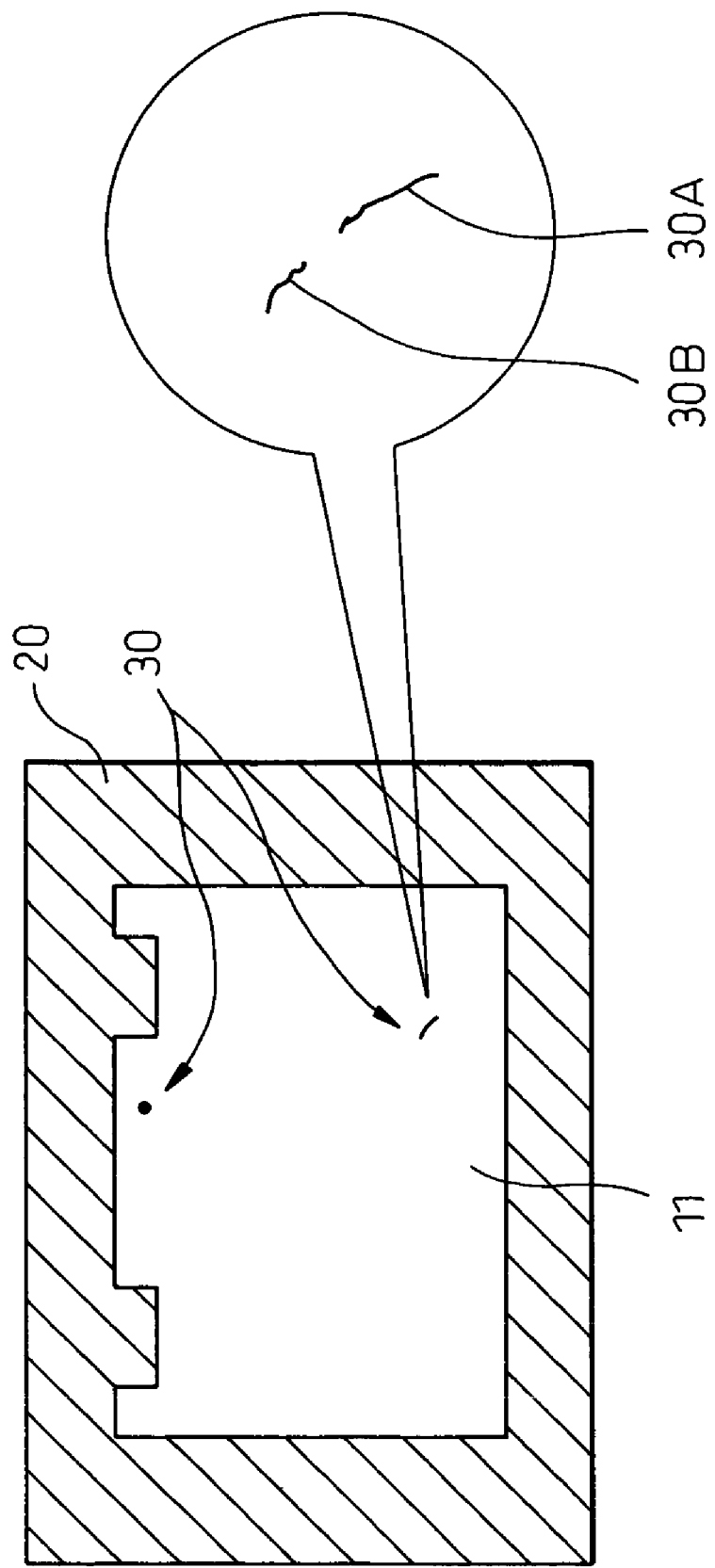

SURFACE INSPECTION METHOD AND APPARATUS

BACKGROUND OF THE INVENTION

The present invention relates to a surface inspection method and a surface inspection apparatus for inspecting the external appearance of an article and, more particularly, to a surface inspection method and a surface inspection apparatus for inspecting for defects on the surface of an article, which is almost flat and continuous but has non-flat parts with small convex shapes and concave shapes, a surface inspection method and a surface inspection apparatus for precisely setting an inspection area to be inspected, and a surface inspection method and a surface inspection apparatus for accurately judging whether a surface is defective.

Conventionally, defects such as flaws on the external surface of an article were inspected visually but recently, defects are inspected by digitally processing images of a surface taken by a video camera. Particularly, in the semiconductor manufacturing process, external appearance inspection apparatuses are widely used to inspect defects of a fine pattern formed on a semiconductor wafer, contributing to the improvement of the yield. In the steel industry etc., inspection apparatuses are used to inspect defects such as flaws on the surface of steel plates conveyed continuously. In contrast to this, the surface inspection method and the surface inspection apparatus according to the present invention are not used in the semiconductor manufacturing process or in the steel industry, but are used to inspect defects such as flaws on the surface of a molded or machined article.

When a surface of an article, which is almost flat, is illuminated, a defective part can be detected because the defective part such as a flaw reflects light in a manner different from the way a normal part does. A surface inspection apparatus for inspecting an article surface comprises an illuminator for illuminating an article surface, an image pick-up device such as a video camera for taking the picture of an article surface, and a processing device for detecting a defective part by digitally processing the image of an article surface and judging whether the article is a conforming one. The processing device is composed of a computer system, which detects a defective part by comparing the image data converted into multi-valued digital data from an image signal with a threshold value set in advance. For example, when a video camera captures light regularly reflected by an article surface, the luminance of a normally flat part is high but the luminance of a defective part such as a flaw is low, therefore, a threshold value lower than a value corresponding to the luminance of the normally flat part is set, and a part, the luminance of which is lower than the threshold value, is judged to be a defective part. If a higher threshold value is set, the number of parts judged to be defective increases and if a lower threshold value is set, the number of parts judged to be defective decreases.

As described above, when an article surface is illuminated, a defective part reflects light in a different manner from that a normal part does, but the difference in the manners light is reflected depends largely on the illumination method. Because of this, various illuminators for surface inspection apparatuses have been proposed hitherto.

Japanese Unexamined Utility Model Application No. 6-76849 has described a configuration in which LED elements are arranged two-dimensionally and a desired illuminance distribution can be obtained by selectively lighting LED elements in accordance with work to be inspected.

Japanese Unexamined Patent Publication (Kokai) No. 2000-171403 has described a surface inspection apparatus for inspecting for defects on the flat surface of an article, which provides an even image in a wide image pick-up area by illuminating the surface so that regularly reflected light enters a video camera (an area sensor camera).

On the other hand, few articles have a flat surface and actually, most articles have an almost flat and continuous surface including non-flat parts with small convex shapes and concave shapes. It is demanded that the surface of such an article can be inspected. However, the manner in which light is reflected by a non-flat part with small convex shapes and concave shapes resembles the manner in which light is reflected by a defective part such as a flaw and therefore, a non-flat part is also detected as a defective part. This means that all the article surfaces are judged to have defective parts and a problem arises in that the inspection is no longer effective.

In order to solve this problem, Japanese Unexamined Patent Publication (Kokai) No. 6-249792 and Japanese Unexamined Patent Publication (Kokai) No. 2000-47369 have described a configuration in which a non-flat part can be prevented from being detected as a defective part by providing a mask to a non-flat part of an image to exclude the non-flat part from the target area to be inspected.

Moreover, Japanese Unexamined Patent Publication (Kokai) No. 10-103938 has described a configuration in which a non-flat part is not detected as a defective part by illuminating an article surface from two or more different angles.

SUMMARY OF THE INVENTION

As described above, various surface inspection methods and apparatuses have been proposed, which inspect an article surface being almost flat and continuous but having non-flat parts with small convex shapes and concave shapes, but the respective methods and apparatuses have respective problems.

According to Japanese Unexamined Patent Publication (Kokai) No. 6-249792 and Japanese Unexamined Patent Publication (Kokai) No. 2000-47369, a non-flat part can be prevented from being detected as a defective part by providing a mask to a non-flat part of an image to exclude the non-flat part from the target area to be inspected, but a problem still remains in that a defective part existing on a non-flat part is not detected.

According to Japanese Unexamined Patent Publication (Kokai) No. 10-103938, a non-flat part is not detected as a defective part by illuminating an article surface from two or more different angles, but a problem still remains in that it becomes more difficult to detect a defective part because the difference between the reflection state of an actually defective part and the reflection state of other parts becomes smaller.

Moreover, when an inspection is made, an article is arranged in an area of illumination under a video camera and the picture of the article surface is taken, but as articles differ in size etc., the area of an article surface in the image differs from article to article accordingly. When a defective part is detected in an image, a processing time required to detect a defective part varies depending on the image size. Therefore, it is preferable for the area to be processed to be limited in accordance with the size of an article surface instead of processing the entire image. Because of this, the inspection area needs to be set conventionally, but this is done only based on the design data. Therefore, if a difference is made between the image of an actual article surface and the inspection area because of the arrangement of the article when the picture thereof is taken, a problem is caused in that there may be a part that is not inspected or an unnecessary part is inspected.

Moreover, the size, length, width, etc., of a detected defective part are compared with evaluation criteria determined in advance and if the data of the part exceeds the evaluation criteria, the article having the defective part is judged to be a rejected (NG) article. However, the position of the part judged to be defective varies depending on the illumination and the set threshold value, therefore, even if a part is judged to be a single continuous defective part by visual inspection, the part may be detected as two or more discrete defective parts. At this time, if the part is a single continuous defective part, the part is judged to be a defect the data of which exceeds the evaluation criteria, but if the part is detected as two or more discrete defective parts, the part may not be judged to be a defect because the data of each discrete part does not exceed the evaluation criteria. As described above, there is another problem in that a defective part cannot be evaluated properly.

A first object of the present invention is to realize a surface inspection method and a surface inspection apparatus capable of detecting a defective part in a non-flat part while not detecting a normal non-flat part as a defective part when an article surface, almost flat and continuous but having non-flat parts with small convex shapes and concave shapes, is inspected.

A second object of the present invention is to realize a surface inspection method and a surface inspection apparatus capable of setting an inspection area accurately.

A third object of the present invention is to realize a surface inspection method and a surface inspection apparatus capable of judging accurately whether a detected defective part is a defect the data of which exceeds the evaluation criteria.

In order to realize the first object described above, a surface inspection method and a surface inspection apparatus according to a first aspect of the present invention correct the image of a non-flat part so that the image is equivalent to that of a flat part. The correction is made by calculating non-flat part correction data for making the image of a non-flat part into an image equivalent to the image of a flat part from the difference between the image of the non-flat part and that of the flat part, and by changing the image of the non-flat part based on the non-flat part correction data. Then, defects on the article surface are detected in the corrected image and whether the surface is a conforming one is judged based on the result of comparison between the data of the detected defect and the predetermined evaluation criteria.

Non-flat parts can be determined based on the design data of an article surface. The correction needs to be made while information indicating a defect is maintained if a detect is present in a non-flat part and, for example, correction data can be calculated from the difference between the average luminance of the images of a non-flat part at two or more points with substantially the same tilt angle and the average luminance of the images of a flat part at two or more points. Due to this, even if the two or more points used for calculation include defects, the influence of the defects is reduced because the defects are averaged, and judgment is therefore not affected.

In order attain the second object described above, a surface inspection method and a surface inspection apparatus according to a second aspect of the present invention detect an edge with respect to the background of an article surface when the image thereof is taken and set an inspection area. If the edge is detected in the entire area of the image, there arises a problem in that the amount of calculations to be processed increases and, therefore, in the present invention, a mask area that indicates without fail the part outside the area of the article surface and an in-work area that indicates without fail the part inside the area of the article surface are set and the edge is detected in the intermediate part between the mask area and the in-work area. Due to this, the amount of calculations to be processed for edge detection can be reduced considerably.

In order to attain the third object described above, a surface inspection method and a surface inspection apparatus according to a third aspect of the present invention make a comparison on the assumption that a detected defect and another detected defect adjacent thereto are regarded as a single defect if the distance between the two defects is within a predetermined value. The adjacent defects can be originally a single defect and it is supposed that the defects are detected as discrete defects because of various conditions, and moreover, regarding the adjacent defects as a single defect is more suitable to the feelings of an observer who actually inspects the defects. Therefore, according to the present invention, judgment can be made in a manner similar to that made by human beings.

According to the first aspect of the present invention, when an article surface almost flat and continuous but having non-flat parts with small convex portions and concave shapes is inspected, defects of the non-flat parts, which cannot be detected conventionally, can be detected and the quality of the inspection is improved.

According to the second aspect of the present invention, with a small increase in the amount of calculations to be processed, the inspection area can be set accurately and the quality of inspection is improved.

According to the third aspect of the present invention, a judgment can be made in a manner similar to that made by human beings and the quality of inspection is improved.

BRIEF DESCRIPTION OF THE INVENTION

The features and advantages of the invention will be more clearly understood from the following description taken in conjunction with the accompanying drawings, in which:

FIG. 3 is a flow chart showing the inspection process in the first embodiment.

FIG. 7A to FIG. 7D are diagrams for explaining the luminance correction of a dip in the first embodiment.

FIG. 8 is a diagram showing a corrected image.

DETAILED DESCRIPTION OF THE PREFERRED EMBODIMENTS

Figure 1:
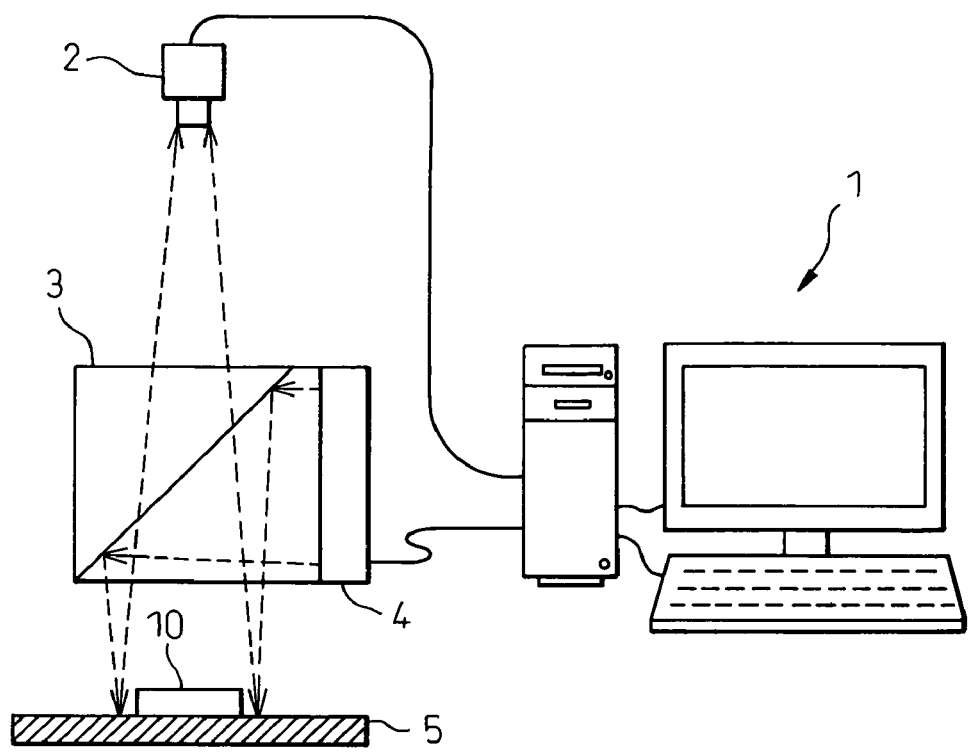
FIG. 1 shows the general configuration of a surface inspection apparatus according to a first embodiment of the present invention.

FIG. 1 is a diagram showing the general configuration of the surface inspection apparatus in the first embodiment of the present invention. As shown schematically, work 10 having a surface to be inspected is placed on a mount 5 and the surface of the work 10 is illuminated with illuminating light from an illuminator 4, being reflected by a beam splitter 3. A video camera 2 captures the image of the surface of the work 10 through the beam splitter 3 and generates an image signal. Hereinafter, the image of the surface of the work 10 is also denoted by reference numeral 10. The image signal is sent to a computer system 1 functioning as a processing device. The computer system 1 has a display and various input devices such as a keyboard, generates image data by digitally converting the sent image signal, and carries out various processes.

Figure 2:
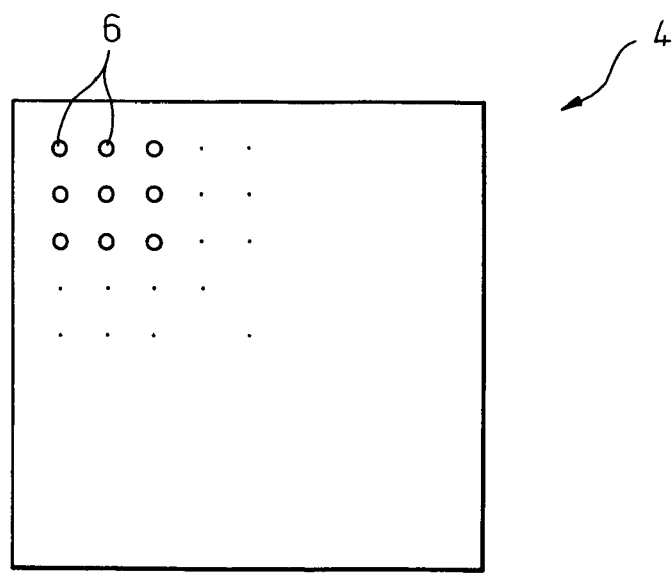
FIG. 2 is a diagram showing an illuminator in the first embodiment.

FIG. 2 shows the illuminator 4. As described in Patent documents 1 and 2, the illuminator 4 has a configuration in which LED elements 6 are arranged two-dimensionally and the illumination area can be changed by selectively lighting the LED elements 6.

The video camera 2 has an optical system with a narrow angle of visibility and is configured so as to capture the illumination light regularly reflected by the surface of the work 10 and the surface of the mount 5. Moreover, the illuminator 4 is configured so that each LED element 6 has directivity to a certain degree and the main light beams, regularly reflected by the surface of the work 10 and the surface of the mount 5, enter the video camera 2. Therefore, flat parts appear bright and non-flat parts with detects such as flaws and convex shapes and concave shapes appear dark in the image of the work surface.

The computer system 1 carries out the process to be explained below on image data and judges whether an article to be inspected is a conforming article by detecting defects.

Figure 4A:
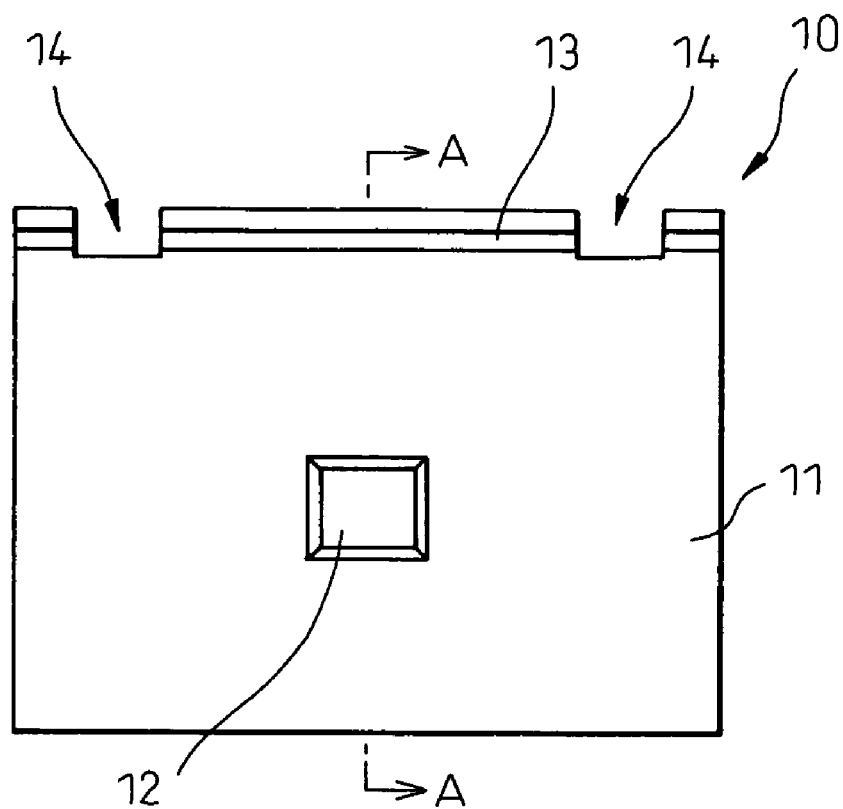
FIG. 4A and FIG. 4B are diagrams showing an example of work used for explanation.
Figure 4B:
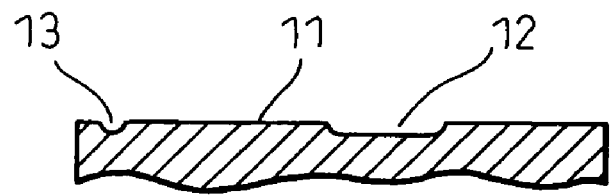

FIG. 3 is a flow chart showing the process carried out by the computer system 1 in the first embodiment. FIG. 4A and FIG. 4B show an example of the work 10 for explaining the process in the first embodiment.

FIG. 4A shows the top surface of the work 10, that is, the image of the work surface, and FIG. 4B is a sectional view of the work shown in FIG. 4A along the A-A line. As shown schematically, the image of the work surface is rectangular in shape and has two cutouts 14. Most flat part 11 of the work surface is almost flat and continuous but the work 10 has a shallow dip 12, rectangular in shape, in the center and an elongate groove 13 provided along the upper side because of the work design. As shown in FIG. 4B, the section of the elongate groove 13 is a part of a circle. Therefore, the part of the sides of the rectangular shallow dip 12 in the center and the elongate groove 13 correspond to non-flat parts.

The process of the computer system 1 in the first embodiment is explained below taking the image of the work surface shown in FIG. 4A as an example.

Figure 5:
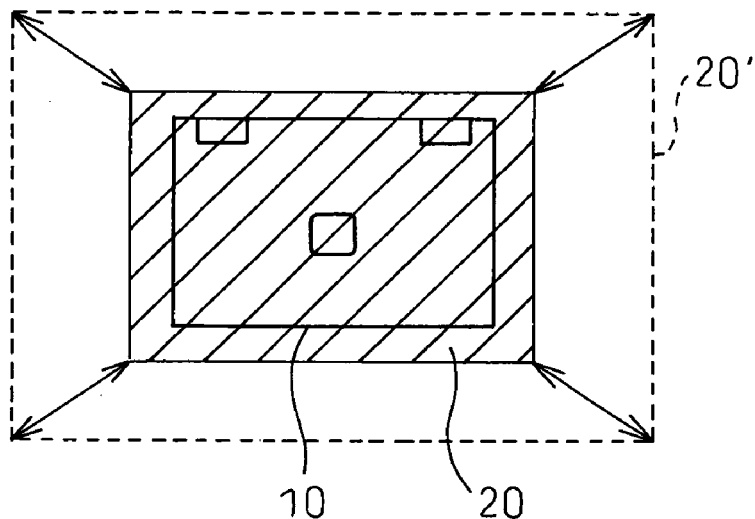
FIG. 5 is a diagram for explaining the setting of an illumination area.

First, in step 101, the size and position of the work 10 are recognized and if the work 10 is located at a great distance from a predetermined position, the position is adjusted. Due to this, an area denoted by 20' is illuminated, as shown in FIG. 5, and an image in which the work 10 is arranged in the center of the area 20' is obtained. In this case, the area 20', which is larger than the work 10, is illuminated and reflection by parts other than the work 10 will adversely affect the detection of defects. Therefore, in step 102, an area denoted by reference numeral 20, which is slightly larger than the work 10, is set as an illumination area.

Next, in step 103, an image is captured.

In step 104, the position of the work in the image is recognized. This process is carried out by, for example, recognizing the position of a predetermined part of the work.

Figure 6:
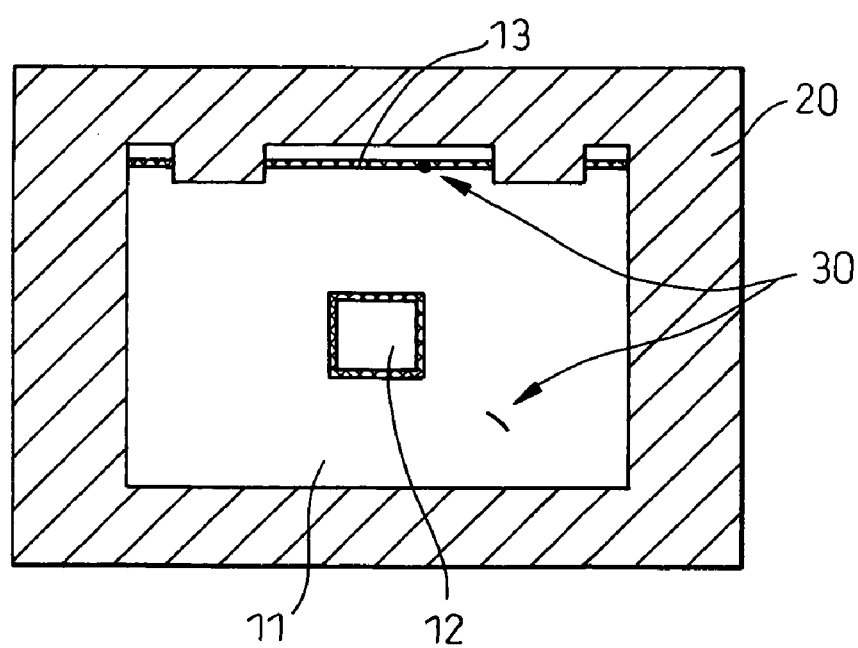
FIG. 6 is a diagram showing an example of an obtained image.

In step 105, an inspection area specified in advance is set based on the detected work position. FIG. 6 shows a state in which an inspection area is set in the captured image. The hatched part 20 indicates an area not to be inspected and the part surrounded by the hatched part is an inspection area, and the surface of this area is inspected. In an example shown in FIG. 6, the flat part 11 and the part inside the rectangular dip 12 in the center appear bright (high luminance), the non-flat parts, that is, the part of the sides of the rectangular dip 12 and the groove 13 parallel to the upper side appear dark (low luminance), and there are flaws 30 on the flat part 11 and in the groove 13, and these parts also appear dark.

In step 106, the shading caused by the optical system and the illuminator 2 is corrected. The shading is corrected based on the amount of shading correction. The amount of shading correction is obtained in advance by capturing an image of a reference surface almost flat and without flaws and calculating an amount that makes the entire surface of the image have the same luminance.

In step 107, non-flat parts provided based on the design data because of the requirements of the specifications of the work are set as a correction area. Here, the part of the sides of the rectangular dip 12 and the groove 13 parallel to the upper side are non-flat parts and an area somewhat larger than the area including these non-flat parts is set as a correction area.

In step 108, the luminance correction data in the correction area is calculated and, in step 109, the luminance in the correction area is corrected by the amount corresponding to the luminance correction data. FIG. 7A to FIG. 7D are diagrams showing an example of a calculation procedure of the luminance correction data, that is, showing an example of a calculation procedure of the luminance correction data in the correction area including the groove 13 parallel to the upper side. As shown in FIG. 7A, the section of the groove 13 is a part of a circle. In FIG. 7A, the groove 13 has the flaw 30 at the edge. The image of the groove 13 appears as shown in FIG. 7B. The image data (luminance) of the groove 13 along the crossing line shown by the arrow 41 in FIG. 7B is shown in FIG. 7C. The luminance rapidly drops at the edge of the groove 13, then temporarily increases in the center of the groove 13, and drops again, and increases rapidly at the other edge.

The groove 13 extends in parallel to the upper side and the sections thereof are all the same shape. Therefore, the image data as shown in FIG. 7C is obtained and the difference from the flat parts other than the groove is calculated. If the luminance in the groove 13 is corrected by the amount corresponding to this difference, the luminance of the groove 13 is the same as that of the flat part 11. Therefore, as shown in FIG. 7D, the image data as shown in FIG. 7C is obtained along the plural lines 42 crossing the groove 13, the average data thereof is calculated, the difference from the flat parts other than the groove is calculated, and the correction data is thus obtained. If there is a defect such as a flaw in the line 42 as shown in FIG. 7D, the precise correction data cannot be obtained, but, by finding the image data along the plural lines 42 and calculating the average data, almost precise correction data can be obtained even if there is a defect in one of the lines 42. By correcting the image of the groove 13 in the correction area by the amount corresponding to the correction data, the image of the part of the groove 13 without a defect is the same image data as that of the flat part 11 and the image of the part of the groove 13 with a defect is corrected for the difference between the groove 13 and the flat part 11 but the difference corresponding to the defect is still kept reserved.

Instead of obtaining the image data about the plural lines 42 as shown in FIG. 7D, it may be possible to obtain the average value of the continuous data corresponding to a predetermined length for each horizontal line along the edge of the groove 13 in the area of the width of the groove 13, calculate the respective differences from the luminance of the flat part, and correct the luminance by adjusting the calculated luminance differences for the pixels on the horizontal line in the entire area in the groove. The length of the horizontal line for obtaining the average value is specified arbitrarily.

In FIG. 7A to FIG. 7D, the correction in the correction area including the groove 13 is explained, and the correction in the correction area including the sides of the rectangular dip 12 is the same. The correction methods are not limited to these examples described above, but any correction method can be accepted provided the difference from the flat part caused by convex shapes and concave shapes is corrected and the difference corresponding to a defect is reserved after correction. The convex shapes and concave shapes are specified by the specifications, and therefore, the size, the sectional shape, the direction, etc., can be predicted based on the design data and it is possible to highly precisely correct the difference from the flat part caused by the convex shapes and concave shapes.

By completing step 109, an image shown in FIG. 8 is obtained. As shown in FIG. 8, the luminance of the sides of the rectangular dip 12 and the non-flat part of the groove 13 parallel to the upper side is substantially the same as that of the flat part 11 but the data of the flaw on the flat part 11 and the flaw 30 in the groove 13 is still kept reserved and the existence thereof can be confirmed.

In step 110, a process of enhancing a defect is carried out on the image, in the inspection area, using plural defect enhancing filters. Further in step 111, a process is carried out for turning the data of the image in the inspection area into two-valued data by comparing the image with a predetermined threshold value. A part the data of which is judged to be equal to or less than the threshold value corresponds to a defect and in FIG. 8, the defect 30 is detected.

The defect detected in step 112 undergoes a labeling process. As will be described later, whether a defect on the surface of work is allowable is judged. In general, a large, conspicuous defect is not allowable but a small, inconspicuous defect is allowable. Because of this, the width, length, etc., of a defect are set in advance as evaluation criteria and the data of a detected defect is compared with the evaluation criteria, and if the data of the part exceeds the evaluation criteria, the work is judged to be a rejected (NG) article. However, the position of the part judged to be defective varies depending on the illumination and the set threshold value, therefore, even if a part is judged to be a single continuous defective part by visual inspection, the part may be detected as two or more discrete defective parts. At this time, if the part is a single continuous defective part, the part is judged to be a defect the data of which exceeds the evaluation criteria, but if the part is detected as two or more discrete defective parts, the part may not be judged to be a defect because that data of each discrete part does not exceed the evaluation criteria. As described above, there is another problem in that a defective part cannot be evaluated properly.

Therefore, in step 113, a labeling link process is carried out and defects adjacent to each other, for example, defects within a predetermined distance of each other are detected as a single defect.

In step 114, for the defect having undergone the labeling link process, the characteristic quantity, that is, the width, length, etc., of the defect, is calculated and, in step 115, the calculated characteristic quantity is compared with the evaluation criteria and, finally, whether the work is a conforming one is judged.

In the first embodiment, the inspection area in step 105 is set based on the design data, but because of the variations in the position at which the work is arranged when the image thereof is taken and in the shape of the work, a difference is produced between the image of the actual article surface and the inspection area, and a problem is caused in that there may be a part that is not inspected or an unnecessary part is inspected. In the second embodiment, this problem is solved.

Figure 9:
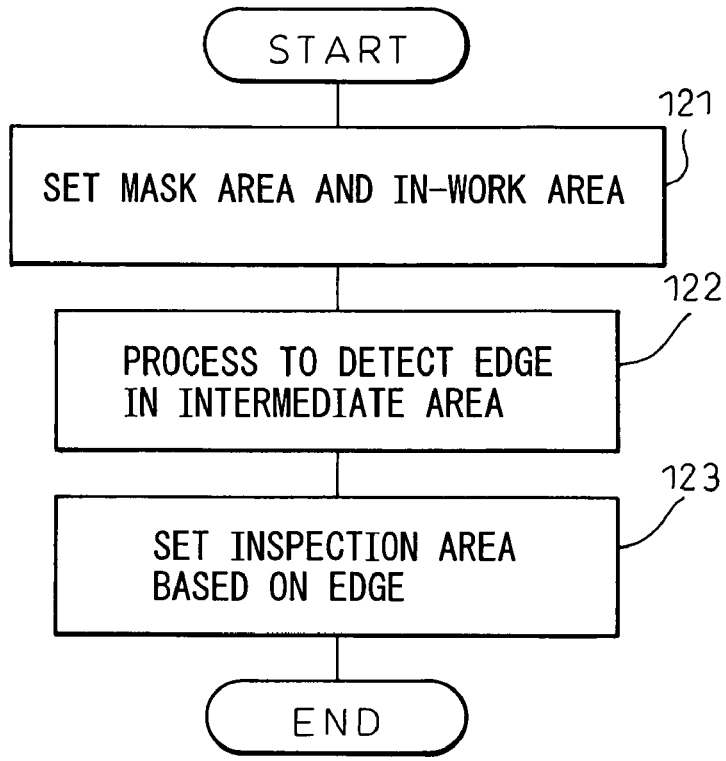
FIG. 9 is a flow chart showing the setting process of an inspection area in a second embodiment of the present invention.
Figure 10:
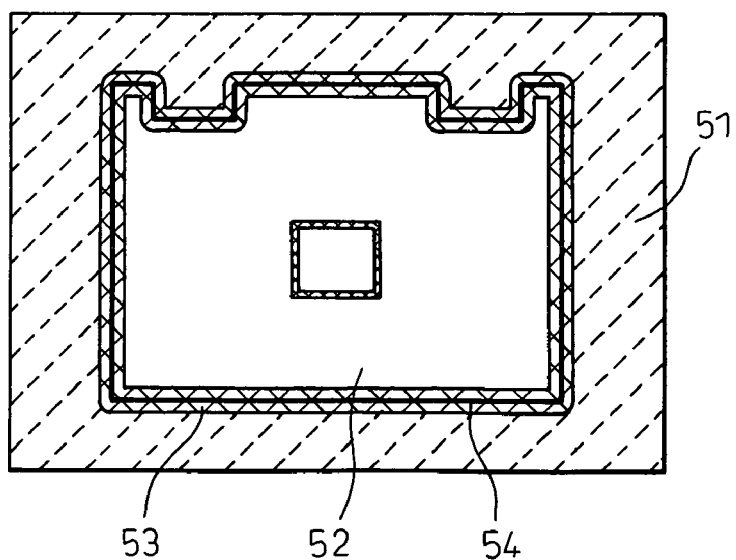
FIG. 10 is a diagram for explaining an edge detection area for setting the inspection area in the second embodiment.

The surface inspection apparatus in the second embodiment of the present invention has the same configuration as that of the apparatus in the first embodiment except for the setting process of the inspection area in step 105. FIG. 9 is a flow chart showing the setting process of the inspection area in the second embodiment. FIG. 10 is a diagram for explaining the setting process of the inspection area in the second embodiment.

In step 121, as shown in FIG. 10, a mask area 51 that indicates without fail the part outside the area of the work surface and an in-work area 52 that indicates without fail the part inside the area of the work surface are set. Then, in step 122, an edge 54 on the work surface is detected in an intermediate part 53 between the mask area 51 and the in-work area 52. In step 123, an inspection area is set based on the detected edge.

According to the second embodiment, as an inspection area is set by detecting the edge 54 on the work surface, even if the work varies in position and shape when the image thereof is taken, an inspection area can be set accurately. Moreover, as the edge is detected in the intermediate part 53 between the mask area 51 and the in-work area 52, it is possible to reduce the amount of calculations to be processed for detecting the edge and increase the processing speed.

The embodiments of the present invention are described above, but it is obvious that there can be various modified configurations other than those described in the embodiments. For example, in the embodiments described above, the video camera captures light regularly reflected by the work surface but it is also possible to make the illumination light enter obliquely with respect to the work surface and not capture the light regularly reflected. In this case, flat parts appear dark and defective parts such as non-flat parts or flaws appear bright.

The present invention can be widely applied to the external appearance inspection of an article the surface of which is almost flat but has parts with convex shapes and concave shapes because of the specifications.

By the application of the present invention, it is possible to inspect for defects at parts with convex shapes and concave shapes present because of the specifications, which are excluded from the target to be inspected hitherto. Moreover, it is possible to properly set an inspection area and properly judge detected defects, therefore, it is possible to ship articles with external appearances of high quality at a reasonable cost.

I claim:

1. A surface inspection method for inspecting for defects on the surface of an article and judging whether the article is to be rejected, the surface being almost flat and continuous, and having a flat part and a non-flat part with convex shapes and concave shapes provided based on design data, the method comprising using a processor to perform the steps of:

taking an image of the article surface;

calculating non-flat part correction data for making the image of the non-flat part into one equivalent to the image of the flat part based on the difference between the image of the non-flat part and the image of the flat part;

correcting the image of the non-flat part based on the non-flat part correction data; and detecting defects on the article surface by processing the image of the article surface after correcting the image of the non-flat part;

wherein the non-flat part is determined based on the design data of the article surface, and wherein the non-flat part correction data is determined by the difference between an average of the image luminance of the non-flat part at plural points having a similar tilt angle and an average of the image luminance of the flat part at plural points.

2. The surface inspection method as set forth in claim 1, further comprising a step of judging whether the article surface is a conforming one based on the result of comparison between the detected defect and predetermined evaluation criteria.

3. The surface inspection method as set forth in claim 1, wherein the image of the article surface is taken while the article surface is being illuminated, and the illumination area is changed in accordance with the size of the article surface.

4. The surface inspection method as set forth in claim 1, wherein detection of defects on the article surface is carried out in a set inspection area.

5. The surface inspection method as set forth in claim 4, wherein the inspection area is determined based on the design data of the article surface.

6. The surface inspection method as set forth in claim 4, wherein a mask area indicating without fail the part outside the area of the article surface is set in the image, an in-work area indicating without fail the part inside the area of the article surface is set in the image, the edge of the article surface is detected in an intermediate part between the mask area and the in-work area in the image, and the inspection area is set based on the detected edge on the article surface.

7. The surface inspection method as set forth in claim 1, wherein detected defects located within a predetermined distance are regarded as a single defect.

8. A surface inspection apparatus for inspecting for defects on the surface of an article and judging whether the article is to be rejected, the surface being almost flat and continuous, and having a flat part and a non-flat part with convex shapes and concave shapes provided based on design data, the apparatus comprising:

an image pickup device for taking an image of the article surface;

a correction data calculation unit for calculating non-flat correction data for making the image of the non-flat part into one equivalent to the image of the flat part based on the difference between the image of the non-flat part and the image of the flat part;

a non-flat part correction unit for correcting the image of the non-flat part based on the non-flat part correction data;

a defect detection unit for detecting defects on the article surface by processing the image of the article surface after correcting the image of the non-flat part; and a non-flat part setting unit for setting the non-flat part based on design data of the article surface, wherein the correction data calculation unit determines non-flat part correction data based on the difference between an average of the image luminance of the non-flat part at plural points having a similar tilt angle and an average of the image luminance of the flat part at plural points.

9. The surface inspection apparatus as set forth in claim 8, further comprising a judgment unit for judging whether the article surface is a conforming one based on the result of comparison between a detected defect and predetermined evaluation criteria.

10. The surface inspection apparatus as set forth in claim 8, further comprising an illuminator for illuminating the article surface, wherein the illuminator is capable of changing the illumination area according to the size of the article surface.

11. The surface inspection apparatus as set forth in claim 8, further comprising an inspection area setting unit for setting an inspection area on the image in which the defect detection unit detects defects on the article surface.

12. The surface inspection apparatus as set forth in claim 11, wherein the inspection area setting unit determines the inspection area based on the design data of the article surface.

13. The surface inspection apparatus as set forth in claim 11, wherein the inspection area setting unit comprises:

a mask area unit for setting a mask area indicating without fail the part outside the area of the article surface in the image;

an in-work area unit for setting an in-work area indicating without fail the part inside the area of the article surface in the image;

an edge detection unit for detecting the edge of the article surface in an intermediate part between the mask area and the in-work area in the image; and an area setting unit for setting the inspection area based on the detected edge of the article surface.

14. The surface inspection apparatus as set forth in claim 8, wherein the defect detection unit regards detected defects located within a predetermined distance as a single defect.

* * * * *